United States Patent [19]
Nelson et al.

[11] Patent Number: 5,331,108
[45] Date of Patent: Jul. 19, 1994

[54] MUTANT MAIZE VARIETY CONTAINING THE GLT1-1 ALLELE

[75] Inventors: Oliver E. Nelson, Cross Plains; David Pan, Madison, both of Wis.

[73] Assignee: Wisconsin Alumni Research Foundation, Madison, Wis.

[21] Appl. No.: 830,038

[22] Filed: Jan. 31, 1992

[51] Int. Cl.$^5$ .................... C12N 15/00; C12N 5/00; A01H 5/00; A01H 1/02

[52] U.S. Cl. .................... 800/235; 800/200; 800/230; 800/250; 800/DIG. 56; 47/58; 47/DIG. 1

[58] Field of Search .................... 435/172.1; 800/230, 800/250, DIG. 56, 235; 47/58.63, DIG. 1

[56] References Cited

U.S. PATENT DOCUMENTS

| | | | |
|---|---|---|---|
| 4,425,737 | 1/1984 | Henke | 47/58 |
| 4,513,532 | 4/1985 | Muirhead, Jr. et al. | 47/58 |
| 4,727,219 | 2/1988 | Brar et al. | 800/1 |
| 4,789,557 | 12/1988 | Friedman et al. | 426/57.8 |
| 5,004,864 | 4/1991 | Robertson et al. | 800/235 |

OTHER PUBLICATIONS

"All Natural Starch Line Displays Unnatural Degree of Activity," Reprint from Prepared Foods (1990).
"Designers Genes: New Varities of Cor . . . Designed Using Contemporary Breeding Technology," Promotional Material from American Maize-Products Co.
Duxbury, D. D., "Modified Stard Functionalities-No Chemicals or Enzymes: 5-Year Genetic Corn Breeding Program Nears Completion," Reprint from *Food Processing* (Dec. 1989).
The Amylograph Handbook, Shuey, W. C. and Tipples, K. H., Eds. (1980).
Coe et al. (1988) In: Corn and Corn Improvement, G. F. Sprague and J. W. Dudley, eds., pp. 139–146.
R. Reiger et al. (1976) Glossary of Genetics and Cytogenetics p. 376.
Weier et al. (1982) Botany pp. 327–344.

*Primary Examiner*—David T. Fox
*Assistant Examiner*—Bruce Campbell
*Attorney, Agent, or Firm*—Quarles & Brady

[57] ABSTRACT

A maize plant has in its genome a non-mutable form of a mutant allele designated vitX-8132. The allele is located at a locus designated as glt which conditions kernels having an altered starch characteristic. Maize plants including such a mutant allele produce a starch that does not increase in viscosity on cooling, after heating.

7 Claims, 1 Drawing Sheet

MUTANT MAIZE VARIETY CONTAINING THE GLT1-1 ALLELE

STATEMENT REGARDING FEDERALLY SPONSORED RESEARCH

This invention was made with United States government support awarded by the Department of Energy (DOE), Grant Nos. DE-FG02-88ER13863 and DE-AC02-82ER12031, and the National Science Foundation (NSF), Grant Nos. DMB-8719615, PCM-8209036, DCB-8507895, and DMB-8811036. The United States Government has certain rights in this invention.

FIELD OF THE INVENTION

The present invention relates generally to genetic manipulations of maize plants and relates more particularly to a specific mutant maize variety and starch produced from this mutant.

BACKGROUND OF THE INVENTION

Maize kernels contain a commercially useful starch, which is a combination of amylopectins and amyloses. Amylose and amylopectin are both polymers of alpha-d-glucopyranose. The polymers differ only in the kind of linkages between glucose residues. Amylose is a linear polymer that has alpha-(1–4) links between adjacent glucose residues, and amylopectin is a branched polymer that contains some alpha-(1–6) links as well. The long amylose and amylopectin polymers store glucose in a semi-insoluble state. Glucose can be obtained by the plant cell by selective degradation of the polymers by specific enzymes.

Maize starch has many food-related applications, such as corn syrups, maltodextrins, dextrins and high fructose corn syrup. Although natural maize starch is useful, much of the starch used commercially today is either chemically or enzymatically modified. The usual purpose of chemical and enzymatic modification of maize starch is to alter the viscosity, texture, heat stability, freeze-thaw stability and other functional qualities of the starch.

There is keen interest today in providing natural maize starches which have the same properties as chemically-modified or enzymatically-modified starches. Use of natural starches eliminates the need for further processing of maize starches. This processing can be quite expensive. Additionally, consumers prefer "natural" food ingredients.

Conventional maize breeding can produce maize with altered corn starch. It was recognized in the 1920's that the "waxy" maize mutant produced altered starch, and maize derived from this mutant was commercially grown in the 1940's specifically for its starch content. Waxy maize produces starch that is nearly pure amylopectin. Maize varieties producing starch with a high amylose content were successfully developed in the 1950's. A great deal of emphasis from the 1950's through until the 1980's has been on improving the techniques for chemical and enzymatic modification of the maize starch.

Identification of a number of mutant maize genes has been the focus of much of the work directed towards creating new varieties of maize for altered starch. Workers have concentrated on the wx (waxy) gene of waxy maize and the ae (amylose extender) gene of high amylose maize. Other genes of interest to maize breeders have been the du (dull), su1 (sugary 1), su2 (sugary 2), fl (flouryl), sh2 (shranken 2), and h (hard or horny) genes. Combinations of these genes in maize have produced starches with a wide range of amylopectin-amyloses ratios, molecular weights and structural characteristics.

Viscosity and viscosity stability are primary criteria for starch applications in food systems. Currently, there is only one available untreated starch with the ability to cool without increasing in viscosity. That instance is a double mutant of dull and waxy, which is limited in use because of its reduced productivity. A starch with this property could be used in certain food products that are heated (for example, baby foods) without the necessity of chemical modification.

SUMMARY OF THE INVENTION

The present invention is a maize plant containing a non-mutable form of a recessive gene conditioning for a vitreous kernel characteristic at a locus designated gltl. A mutant gene at that locus has been designated gltl-1. Such a corn plant is capable of producing a modified starch. The modified starch has the characteristic of not increasing in viscosity when the heated starch is cooled.

The present invention is also a method of creating a maize plant capable of producing a starch with the characteristic of not increasing in viscosity when cooled. This method comprises crossing a first and a second plant, where both of the plants are homozygous for the gltl-1 gene.

It is an object of the present invention to provide a maize plant containing the gltl-1 gene.

It is another object of the present invention to provide a maize plant capable of producing a modified starch. An advantage of the present invention is that the starch from this mutant maize plant does not increase in viscosity upon cooling. This characteristic is useful in certain food-preparation applications.

Other objects, advantages, and features of the present invention will become apparent from the following specification when taken in conjunction with the accompanying drawings.

DESCRIPTION OF THE PREFERRED EMBODIMENT

Figure 1:
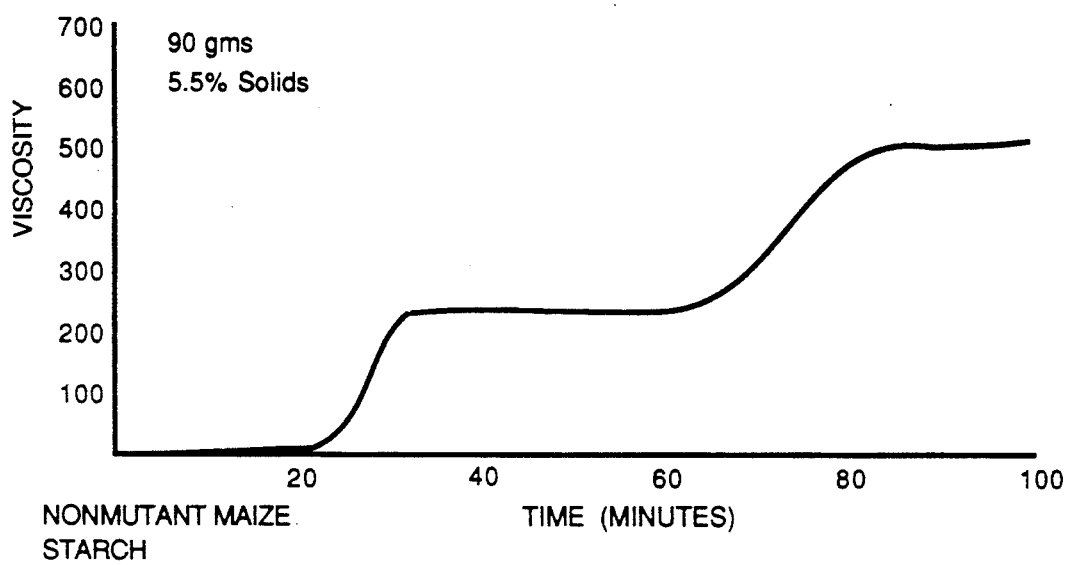
FIG. 1 is a Brabender plot of the viscosity change upon heating and cooling of non-mutant maize starch.

The present invention is directed toward a maize plant comprising in its genome a non-mutable mutant defective allele at the newly identified gltl-1 locus, and also toward starch derived from such a maize plant. An exemplary defective mutant allele at this locus, here designated gltl-1, has been identified and is made available for introduction into any desired line of maize plant. A maize plant containing the gltl-1 allele has been deposited as ATCC Accession No. 75122. A maize plant of any desired genetic background containing the gltl-1 gene may thus be created by repeated back-crossing of a maize plant of the desired genetic background with a maize plant of the deposited line. Alternatively, an alternative mutant allele for the trait may be created by a maize breeding program as disclosed below.

The gltl locus of the gltl-1 gene is located on the short arm of chromosome 4, as shown by crosses with a series of B-A translocations. As indicated by the laboratory symbol, gltl, the mutant allele is recessive.

The phenotype by which the gltl allele is easily identified in segregating progenies is the deep dimpling of the crown and a vitreous appearance of the kernel. Vitreousness is apparent in the deposited seed sample, but is not always retained in other genetic backgrounds. The homozygous mutant seeds (gltl-1/gltl-1) are readily visually identifiable by the deep dimpling and, in addition, weigh on the average only 81% as much as non-mutant seed. The kernels in the deposited seed sample also have a pronounced orange color. In outcrosses to other lines followed by recovery of mutant kernels, the dimpled phenotype and orange color are sometimes separated, suggesting that the orange color may be attributable to a linked gene.

The gltl-1 mutant gene can be easily transferred to other genetic backgrounds or inbreeds by successive crosses to a recurrent parent of any desired genetic background. The plants in the backcross progenies which are heterozygous for the mutant gene can be identified by self-pollinating the plants and ascertaining which plants are segregating for the dimpled seed phenotype. After the requisite number of backcrosses to the recurrent parent, the mutant seeds segregating in the heterozygous parents are to be saved. These seeds constitute a gltl version of the genetic background of the recurrent parent. It would be prudent to check the type of starch being produced by the partially converted gltl lines at several points during the backcrossing process to insure that there is not an unfavorable interaction between the gltl mutant and the genetic background into which it is being crossed that would alter the type of starch that gltl conditions in its present background.

We have deposited maize seed containing the gltl-1 mutation. These seeds were deposited with American-type culture collection, Rockville, Md., on October 9, 1991, as Accession No. 75122. These seeds were obtained from a breeding program described below, and exhibit the characteristic gltl phenotype of a dimpled crown, vitreousness and a pronounced orange color.

Starch from other crosses containing the gltl gene may exhibit some variation from the starch disclosed in the example below.

The particular usefulness of the starch produced from a glt/glt maize plant has to do with its viscosity in relation to temperature change. A standard test used to measure these viscosity characteristics is known as the Brabender test. The Brabender test is performed using an instrument known as an amylograph, a model of which is made by the C. W. Brabender Instrument Co. The test, and the instrument, are described in *The Amylograph Handbook*, Schuey & Tipples, Ed., (1982) from the American Association of Cereal Chemists, St. Paul, Minn. In brief, in the test a sample of cereal starch is heated in the presence of water to determine when the hydration and swelling of starch particles begins, due to breakdown of hydrogen bonds. This swelling, referred to as gelatinization, is accompanied by a measurable increase in viscosity of the starch paste. While prolonged heating following gelatinization would break down the particles, leading to a decrease in viscosity, if the temperature of the paste is decreased shortly after gelatinization, the cooling starch paste will typically increase again in viscosity as the particles begin to associate. The output of the Brabender test is a curve of viscosity over time, taken while temperature is first increased over the gelatinization temperature (typically to about 90°–95° C.) and then decreased. The Brabender curve is typically analyzed to determine gelatinization temperature, maximum viscosity on cooking, viscosity increase on cooling, and maximum cold viscosity. These data points are characteristic of the quality of the starch. For typical corn starches, the gelatinization temperature is in the range of 62°–72° C., and the starches sharply increase in viscosity upon cooling. Thus to test for increase, or lack of increase, in viscosity upon cooling, the starch paste must first be heated over the range of about 62°–72° C., and then cooled.

The corn starch from maize which was homozygous glt/glt behaves anomalously in the Brabender test. Like normal corn starch, starch from these plants does increase in viscosity when heated, but unlike normal corn starch, it does not again increase in viscosity when cooled. This makes corn starch with this unusual characteristic advantageous for certain food applications, such as baby food, where high viscosity is not desired. While corn starch from normal corn plants can be chemically modified to behave in this fashion, no other single mutant maize mutants have been reported to yield starch having this characteristic.

As discussed further below, there are indications that the gltl mutant genotype conditions for a defective bifunctional glucosidase-transferase enzyme. The developing mutant endosperms have been found to have very low activity, less than 10% of wild type, of a bifunctional enzyme that is capable both of cleaving alpha-1,6-glucose linkages, as demonstrated by its ability to attack pullulan with a release of maltotriose, and of transferring oligosaccharides from a 14C-labelled donor to an unlabelled acceptor, or vice versa.

The hypothesis that the gene at the gltl locus encodes for a bifunctional enzyme partially responsible for starch synthesis has been supported by the research results to date. Extracts of mutant endosperm have a much diminished capacity to produce reducing sugars from the fungal polysaccharide, pullulan, compared to non-mutant endosperm. Analysis of products of pullulan metabolism by the non-mutant enzymatic action reveal that primarily α-1,6 linkages are attacked.

The enzymatic activity varied directly in proportion to the number of non-mutant genes present. Heterozygous endosperm fractions yield enzymatic activity intermediate between homozygous mutant and homozygous non-mutant endosperm extracts. The relationship appears linear.

The transferase activity was demonstrated by the ability of the enzyme to transfer from phytoglycogen to [$^{14}$C] maltose and to incorporate [$^{14}$C] glucose into β-limit dextran or amylose. The transferase activity co-purified with the glucosidase activity through all purifications performed.

The molecular weight of the glucosidase-transferase enzyme has been estimated at 89,000 dalton by elution from a Sephadex G/50 columns in conjunction with molecular weight standards.

If the gene does indeed express a mutant defective enzyme, this suggests strongly that other similar mutant defective alleles at the same gltl locus can also be created by mutagenesis and screening of maize stocks. By exposing maize kernels to random mutagenic agents, such as EMS or radiation, numbers of randomly mutant offspring can be created. By screening such mutant progeny for the phenotype of the dimple appearance, and by crossing the presumed mutant to a glt/glt line to test as to whether the newly created mutant will complement the authentic mutant, the nature of the new allele can be verified. Such new mutant alleles would have the benefit of likely having virtually no mutability, since the occasional mutability remaining in the present gltl-1 allele appears to result from its origin as an insertion of a transposable element. Such techniques of mutagenesis and screening are well known to those of ordinary skill in the art. Accordingly the means and the motivation exist to create other stable mutant alleles at the gltl locus which would condition a similar starch phenotype to the gltl-1 gene described here.

EXAMPLES

The mutant maize plants experimentally designated gltl/gltl were created through a series of breeding steps described below. The aim was to create a mutant maize capable of producing an altered starch which would retain the gltl mutant characteristic but which would lack somatic "mutability." By somatic mutability, it is meant the characteristic of reverting back to a non-mutated form. Evidence of mutability is the occurrence of kernels that lack, at least in part, the mutant phenotype. Evidence of somatic mutability can occur within an individual kernel, which may have sectors that have reverted. When a plant lacks mutability, it is meant that the vast majority of kernels have not reverted. A mutant maize lacking mutability is advantageous because the maize crop production would be uniform from generation to generation.

Year 1: An ear of corn was received with both mutant and non-mutant kernels. The mutant kernels were distinguishable because they were deeply dimpled on the top surface. The mutation was investigated solely based on its unique and interesting phenotype.

The mutant kernels were planted in Row 25682. The resulting plants were self-pollinated and two ears were produced. The kernels on both ears showed evidence of somatic mutability, the evidence being the presence of sectors of apparently non-mutant tissue. Testcrosses of these plants onto maize plants with mutations at amylose extender, dull, and sugary-2 loci showed that this mutant was not allelic to any of these mutants, which were the most likely candidates for known loci of mutant alleles which might condition this mutant phenotype.

Year 2: Kernels from 25682-2[X] that did not show evidence of mutability were planted in Row 27228. These plants were self-pollinated, and four ears were obtained. All kernels on the four ears showed mutable sectors.

Tests were made to determine where on the maize chromosomes the mutant gene was located. To that end, kernels from 25682-2[X] were planted in rows 27558-27561, and the plants crossed by a series of B-A translocations. The results (mutant kernels appearing in the cross by +/TB-4Sa) showed that the mutant gene is located on the short arm of chromosome 4.

Year 3: Because sugary-1 locus is also located on the short arm of chromosome 4, it was decided to test whether or not the mutant was identical to the sugary-1 mutation. Kernels from 27228-1[X] were planted in Row 29239. Testcrosses by a sugary-1 tester (a maize plant with a mutation at the sugary-1 locus) showed that the mutant is not a sugary-1 allele. Three selfed ears were obtained. The phenotype of the kernels of these ears were phenotypically like some sugary-2 lines, but somatic mutability was apparent on most kernels. There were no obvious germinal mutations.

Year 4: The seeds from the Year 3 crop (29239[X]) were designated vitX-8132. These seeds were planted in Row 35358 and crossed by Row 35353, which was W22Nr-g, a derivative of the common inbred line W22N. W22Nr-g maize was used as an inbred background into which the mutant could be crossed to observe the mutation in a standard background for convenient comparison to other mutants in the same background.

Four self-pollinations were also performed. On all resulting ears, there were kernels with mutable sectors, but also kernels with no overt somatic mutability.

Year 5: The F1 seed from the cross of the previous year (vitX-8132/W22Nr-g) was planted in Row 37312. The F1 plants were self-pollinated. Three of the selfed ears had no or limited evidence of mutability. However, on one ear saved, 37312-1[X], there was at least one kernel showing somatic mutability. Another ear (37312-2[X]) showed clear evidence of mutability. Kernels without apparent mutable sectors from 35358-1[X] were planted in Row 37313. The resulting plants were self-pollinated. From the self-pollinated plants, six ears had kernels showing non-mutant sectors. One small ear did not have any kernel with apparent non-mutant sectors. Kernels with clear mutability from the same ear, 35358-1[X], were planted in Row 37314. The nine ears from the selfs from this row all had some kernels with non-mutant sectors.

Year 6: The vitX-8132 kernels from 37312-1[X] were planted in Homestead, Florida in Row F8830 for a winter crop. On four of the ears from the resulting selfs, there were kernels with discernible somatic mutability. One self (F8830-1[X]) did not have any kernels with apparent mutable sectors.

Kernels from F8830-1[X], now designated as vitX-8132 (W22N[1]), were planted in Row 39057. After self-pollination, eight ears were obtained. There was no indication of mutability on these ears. Kernels from 37312-1[X], which were noted as having no non-mutant sectors, were planted in Row 39324. Self-pollination occurred and two resultant ears both had some kernels displaying somatic mutability.

There was also a cross by Row 39020 (W22N r-q).

Year 7: The vitX-8132 (W22N[1]) kernels from 39057[X] were planted in Row 41214. The plants were selfed and testcrosses made for each to ascertain whether any plant had an active Activator (Ac) or Suppressor-mutator (Spm) transposable element. All tests for these transposable elements were negative. These tests indicated that although the observed mutant gene seemed mutable, suggesting a transposon, the transposon was neither Ac nor Spm.

The seed from the cross of 39324 by 39020 [vitX-8132 (W22N[1])/W22N] was planted in Row 41286. Of the seven ears resulting from self-pollination, three had kernels with mutable sectors, and four did not. The mutant kernels resulting from these selfs were now designated as vitX-8132 (W22N[2]).

Year 8: The mutant kernels from 41286[X] were planted in Row 43454, and the plants were selfed.

Starch Analysis

Starch was analyzed from vitX-8132 (W22N[1]) seed grown in row 39057 in Year 8. The results of these tests are reported in FIGS. 1 and 2. Starch was also tested from seed from 41214[X] and the results confirmed the earlier tests. (The row 41214[x] was planted with seed from 39057[X].)

The Brabender tests were performed as described in the *Amylograph Handbook, supra.*

Figure 2:
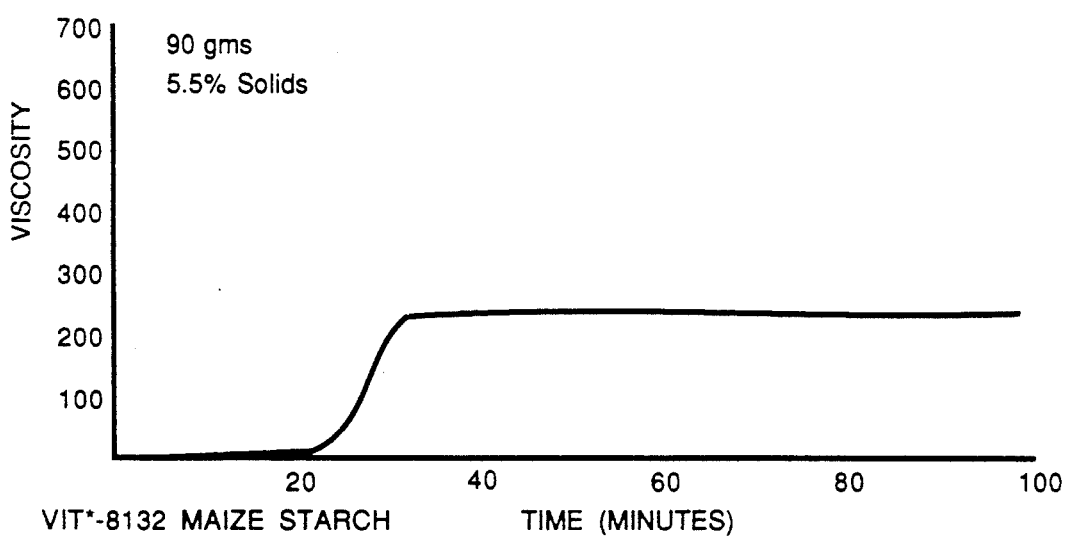
FIG. 2 is a Brabender plot of the viscosity change upon heating and cooling of starch from maize containing the vitx-8132 gene, which is now being designated gltl-1.

FIGS. 1 and 2 represent the result of a Brabender test. The Brabender test examines the rise in viscosity of the starch upon heating and the further change in viscosity upon subsequent cooling. Starch from these mutant maize plants behaved differently than standard starch in that no increase in viscosity was observed upon cooling, as can be determined by comparing FIG. 1 (control) with FIG. 2 (gltl-1/gltl-1). Note in the curve of FIG. 2 that there is no second rise in the curve. This represents a lack of increase in viscosity upon cooling.

Enzymatic Analysis

Following analysis of the enzymatic activity of non-mutant endosperm as compared to endosperm containing the mutant allele originally designated vitX-8132, it was determined that the allele was associated with deficiencies in the glucosidase and transferase activities. Hence the locus was designated gltl and the recessive mutant defective allele was designated gltl-1.

Considerable information concerning the enzymatic lesion in gltl-1 has been developed. A bifunctional enzyme that cleaves both alpha-1,6-glucose and alpha-1,4-glucose bonds and has the additional capability of transferring the maltose or maltotriose units released to acceptor oligosaccharides or polysaccharides is markedly reduced in mutant maize endosperms and increases in a linear fashion with increasing numbers of non-mutant alleles in the endosperm. The enzyme appears similar to the glycogen debranching enzyme from rabbit muscle investigated by the Browns in the 1960's, but the presumption was that the enzyme was concerned only with the hydrolysis of glycogen.

We claim:

1. A maize plant comprising in its genome the gltl-1 mutant allele, wherein the gltl-1 mutant allele is derived from plants of the line deposited as ATCC No. 75122.

2. Seed of the plant of claim 1.

3. A maize plant comprising in its genome a gltl-1 mutant allele at the glt locus which conditions for a maize kernel, the starch from which plant does not increase in viscosity upon cooling, after being heated over 72° C., wherein the gltl-1 mutant allele is derived from plants of the maize line deposited at ATCC No. 75122.

4. Seed of the plant of claim 3.

5. A method for producing a maize plant capable of producing a starch that does not increase in viscosity upon cooling after being heated over 72° C., the method comprising crossing first and second maize plants, where both of the maize plants contain the gltl-1 mutant allele, wherein the gtlt-1 mutant allele is derived from plants of the line deposited as ATCC No. 75122.

6. The method of claim 5 wherein both of the first and second maize plants are grown from ATCC No. 75122 seed.

7. A plant produced by the method of claim 5.

* * * * *